United States Patent [19]

Clark

[11] Patent Number: 4,564,274

[45] Date of Patent: Jan. 14, 1986

[54] VISIBILITY GAUGE

[75] Inventor: Barry A. Clark, Heidelberg, Australia

[73] Assignee: The Commonwealth of Australia, Australian Capital Territory, Australia

[21] Appl. No.: 320,133

[22] Filed: Nov. 10, 1981

[30] Foreign Application Priority Data

Nov. 13, 1980 [AU] Australia .............................. PE6488

[51] Int. Cl.⁴ .............................................. A61B 3/00
[52] U.S. Cl. .................................. 351/233; 351/222; 351/246
[58] Field of Search ............... 351/233, 222, 234, 235; 350/3.81, 321, 431

[56] References Cited

U.S. PATENT DOCUMENTS

| | | | |
|---|---|---|---|
| 2,313,240 | 7/1940 | Hubbard | 351/233 |
| 2,379,103 | 11/1943 | Rath | 88/23 |
| 2,484,735 | 10/1945 | Rath | 88/23 |
| 2,528,513 | 11/1950 | Grether . | |
| 2,770,164 | 11/1956 | Olmsted et al. . | |
| 2,955,507 | 10/1960 | Leitz . | |
| 3,415,594 | 12/1968 | Aulhorn . | |
| 3,436,840 | 4/1969 | Noxon | 350/314 UX |
| 3,599,545 | 8/1971 | Durr | 95/10 |
| 4,192,995 | 3/1980 | Anthon | 250/338 |

FOREIGN PATENT DOCUMENTS 2528885  4/1977  Fed. Rep. of Germany .
1589714  5/1981  United Kingdom .

OTHER PUBLICATIONS

Luckiesh, Test Charts Representing a Variety of Visual Tasks, 3/1944, Amer. Journal of Opthal.

Primary Examiner—Rodney B. Bovernick
Attorney, Agent, or Firm—Stevens, Davis, Miller & Mosher

[57] ABSTRACT

A visibility gauge in the form of a disc or strip of diffusing material arranged to be interposed in the light path from a subject to an observer. The diffusiveness of the strip varies along its length so that the contrast between the subject and its background can be selectively varied by arranging the strip to transmit progressively greater or smaller proportions of diffused light until a threshold of visibility is reached. The strip may be in the form of a wedge of diffusing material or a clear strip with one surface treated to be progressively more diffusive towards one end.

1 Claim, 1 Drawing Figure

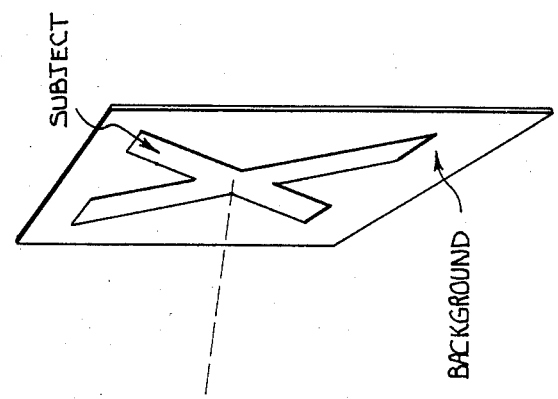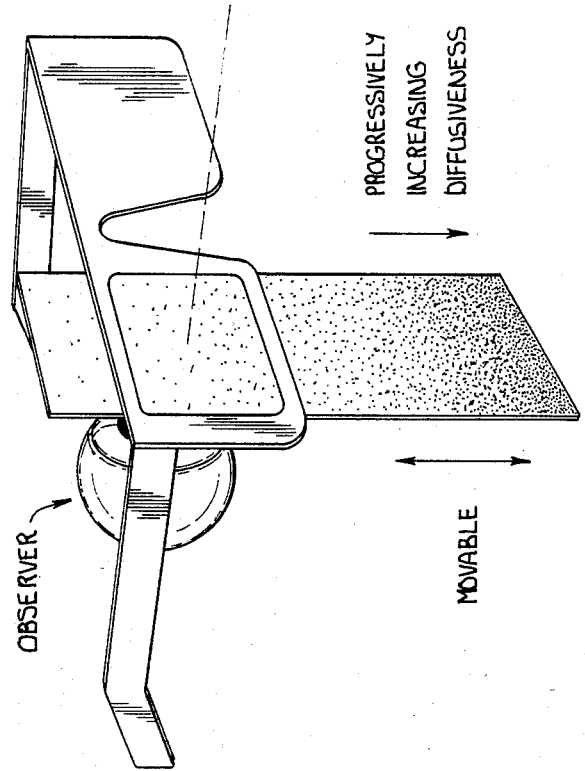

VISIBILITY GAUGE

This invention relates to visibility gauges for determining the visibility of a subject by varying the contrast between the subject and a back ground until a threshold is reached. Such visibility gauges may also be used for determining the sensitivity of an observer's eye by using a standard subject and background under standard illumination and increasing the contrast until the subject is identifiable to the observer. The invention also relates to methods of using and of manufacturing such gauges.

The visibility of a subject,—e.g., the legibility of written or printed characters—depends upon the size of the subject, the amount of light and the contrast between the subject and its background. The present invention relates to measuring the combined effects of these variables. The invention is particularly useful for determining legibility which is an important criterion in designing for example instrument panels, traffic and advertising signs and in determining print sizes for the visually handicapped.

A graded neutral density filter has been used in the past to determine visibility but this works by progressively reducing the amount of light reaching the eye. While the amount of light necessary to distinguish a subject does vary depending on the contrast this method assumes that the human visual system works similarly over a range of light levels and this is not necessarily a valid approximation.

Another known visibility measuring device is a visibility meter which reduces a subject's visibility to threshold by reducing the contrast by superimposing a veiling luminance. The veiling luminance is provided by either the task background or a standard reflecting surface placed beside the task or by an internal light source. The observer views the task directly through a variable beam splitter with no lenses. The variable veiling luminance is provided by reflecting a portion of the task background or the standard surface, from the beam splitter and focusing it at the eye with a single lens. The effect is the same as if the whole area of the focusing lens were the source of the veiling luminance. The task is reduced to threshold by increasing the transmission density of the variable beam splitter while simultaneously increasing the veiling luminance. The beam splitter may be a piece of glass with varying amounts of chromium alloy vapor-deposited on it.

In another known meter unfocused veiling light is reflected by a front-silvered mirror to rotating discs where it is reflected by the front aluminized surfaces to the observer's eye. The rotating discs consist of two aluminized discs which can be moved relative to one another while they both rotate on the same spindle and at the same speed. Direct light from the subject is transmitted through radial apertures cut in the discs while veiling light is reflected from the front aluminized surface. Relative motion between the two discs, and therefore the ratio of transmitted to veiling reflected light is controlled and a visibility threshold determination is made by rotating the discs at a constant speed while adjusting the ratio of transmitted to reflected light by relative movement of the discs until the threshold condition is achieved.

These visibility meters are relatively complex and expensive. Also their bulk is a disadvantage where testing of visibility in confined work spaces is required, such as in an aircraft cockpit.

An object of the present invention is to provide a relatively simple and inexpensive visibility gauge. A further object is to provide a visibility gauge which can be quite compact. Yet other objects are to provide a method of using such a gauge and a method for manufacturing such a gauge.

According to the present invention there is provided a visibility gauge for determining the visibility of a subject by varying the contrast between the subject and a background characterised by diffusing means arranged to be interposed in a light path between the subject and an observer, the diffusing means having different portions arranged to be interposed in the light path and to direct different proportions of scattered light from the subject and its background to the observer. The different portions need not be separate components, but they may all form part of single diffuser, e.g. one which varies in diffusiveness from one extreme to another so that a different diffusion effect is achieved at different locations between those extremes. The variation in diffusiveness may be progressive or it may occur in steps which may or may not be regular.

Other details and features of the invention will stand out from the description given below by way of non-limitative example and with reference to the accompanying drawing.

The drawing shows a diffusing member in the form of a strip mounted in a supporting spectacles frame. Successive portions of the diffusing strip have different diffusiveness. The strip is movable to locate the successive portions in the light path from the subject to the observer.

In the preferred arrangement the diffusing means comprises a diffusing member movable through a plurality of positions in which successive portions of the diffusing member ranging from a minimum to a maximum diffusion portion are interposed in the light path so that progressively higher proportions of scattered light from the subject and its background are directed to the observer.

The diffusing member may be a reflector, successive portions of which are interposed in the light path and which are arranged to diffusely reflect progressively more incident light than is specularly reflected. However, preferably the diffusing member is constructed for transmitting to the observer progressively more diffused light than light which is passed straight through the member to the observer.

For a transmitting member the total light transmittance for all portions is preferably as large as practicable and approximately constant so that no substantial change of adaptation of the observer's eye to different light intensities takes place when the successive portions are interposed in the light path. For example the total transmittance (directly transmitted light and diffusely transmitted light) may be about 80%. Preferably the total light transmittance difference between the minimum and maximum diffusion portions of the diffusing member is not more than about 10%. With these transmittance values eye adaption in the photopic range of light intensities (i.e. twilight and daylight conditions) is not substantially affected. Even small differences in total transmittance may be compensated by progressively increasing the light absorption of the material of which the diffusing member is made towards the minimum diffusion portion so that, for example, a 5% increase in transmittance caused by less diffusion is balanced by a 5% increase in absorption by the material itself. The progressive change in absorption by the material may be achieved by staining the material and progressively increasing the thickness of the member towards the minimum diffusion portion or by providing the material with a semi-transparent coating which is progressively more absorbent towards the minimum diffusion portion.

The diffusing member may be of any suitable configuration. For example the member may be in the form of a rotatable disc having a circumferential portion of progressively increasing diffusiveness so that rotation of the disc with the circumferential portion in the light path interposes portions of differing diffusiveness in the light path. Alternatively, the diffusing member may be in the form of a strip having the successive portions of increasing diffusiveness along its length.

The diffusing member may be mounted in a supporting frame which may be in the general form of a spectacles frame. The frame may have a cover member for covering one of the observer's eyes and the diffusing member is mounted so as to be progressively movable to locate the successive portions over a viewing aperture in front of the other eye. One diffusing member of sufficient size or two diffusing members suitably coupled together may be arranged for viewing with both eyes if this is considered desirable.

The successive portions of the diffusing member that are interposed in the light path may be comprised by a series of portions of discretely different diffusiveness. Alternatively there may be a continuous increase in the diffusiveness of the member throughout its range of positions.

The positions of the diffusing member at the point where the contrast between the subject and its background render the subject indistinguishable may be used as a measure of the visibility of the subject. This measure may be derived by providing the diffusing member with a plurality of graduations which are movable with the member past a fixed pointer or by providing a pointer movable with the diffusing member and arranged to indicate against a fixed plurality of graduations. The reading from the scale consisting of the graduations may provide a qualitative measure of the subject visibility or the scale may be calibrated against some standard enabling quantitative measures of visibility.

When used for determining the sensitivity of an observer's eye, a standard subject and background under standard illumination may be viewed through the diffusing member. For example the diffusing member could be incorporated in optometrist's or ophthalmic apparatus for testing a patient's eyes. The diffusing member may be in the form of a disc which can be rotated to progressively reduce the proportion of diffused light transmitted to the patient's eye so that the point where the subject becomes recognizable would provide information on the sensitivity of the patient's eye.

In one possible construction, the diffusing member is in the form of a wedge of diffusing material so that the thicker end of the wedge will transmit a higher proportion of diffused light than the thinner end. For example a layer of a translucent substance such as milk between two glass plates which define a wedge shaped cavity between them may constitute the diffusing member. Alternatively the diffusing member may be in the form of a wedge of clear material having diffusing particles suspended in the material, the particles being of substantially constant concentration throughout, so that the thicker end of the wedge will transmit a higher proportion of diffused light. Such a wedge may be provided using the Kalliroscope effect which results from diffusion by a plurality of crystals of a certain refractive index suspended in a clear material of different refractive index.

In another possible construction, the strip is made of a clear material and is of substantially constant thickness along its length, diffusing particles being suspended in the clear material, the density of the particles changing progressively from one end of the strip to the other.

However, in the simplest construction envisaged, the diffusing member is a constant thickness clear strip (or disc) having one surface treated so as to diffuse progressively more light towards one end. The surface may be treated by etching, scoring or abrading. Etching may be achieved by providing a photo-resist pattern on the strip surface, the pattern being arranged so that progressively more of the surface is etched towards one end so that that end diffuses more light. In the preferred embodiment, the surface is abraded such as by sand blasting. Whichever method of surface treatment is chosen it is preferred that at least some of the original strip surface is not disturbed even at the maximum diffusion end of the strip, enabling some light to be transmitted directly through all portions of the member.

This method of determining the visibility of a subject according to the present invention includes the steps of arranging the visibility gauge so that the diffusing means is interposed in the light path between a subject and observer and selectively moving the diffusing means until the contrast between the subject and its background reaches a threshold. The maximum diffusion portion may be initially interposed in the light path and the diffusing member moved so that progressively less diffused light and progressively more direct light reaches the eye until the point where the subject is identifiable is reached. The reverse operation may be used if desired.

As mentioned above the diffusing member may be a transmitting strip or disc with the surface treated so as to be progressively more diffusive towards one end or around its circumference. The method of preparing the diffusing member according to the present invention comprises subjecting successive portions of a transparent member to a substantially constant force and density of abrasive particles for successively longer times to produce a progressive change in diffusiveness.

This may be achieved automatically by passing the member through a stream of abrasive particles at a progressively changing speed so that each successive portion is subjected to the abrading action for a progressively different time.

Alternatively the method may be performed manually. For example a transparent member in the form of a elongated strip may be mounted over and spaced above an elongated member bearing a plurality of characters which are visible through the strip. A hand-held blasting nozzle may be passed along the strip until the characters can be seen through progressively more diffusive strip material from one end to the other.

The strip may be of any suitable material such as poly(methyl methacrylate) (sometimes known as perspex). The abrasive particles may be small approximately spherical glass beads which are used in some types of blasting apparatus.

The abrasive particles form small pits in the surface of the transparent member to impart the diffusive properties. Preferably some portions of the strip surface are left unpitted even at the most diffusive portion so that direct transmittance of some light rays is possible.

The diffusing member constructed by any method of surface treatment may be used itself for the purpose of visibility measurement or it may be used as a master for the production of replicated diffusing members by any suitable process or casting, moulding or hot pressing.

Finally, it is to be understood that various alterations, modifications and/or additions may be introduced into the construction and arrangements of parts previously described without departure from the spirit or ambit of the invention as defined in the appended claims.

I claim:

1. A method of determining the visibility of a subject against a background thereof, comprising arranging a visibility gauge including a diffusing member so that the diffusing member is interposed in a light path between a subject and an observer at a position near to the observer so as to be out of focus, the diffusing member having different portions arranged in succession and operative to transmit progressively differing proportions of scattered light from the subject and its background therethrough, the total light transmittance for all said different portions being approximately constant so that no substantial change of adaptation of the observer's eye to differeng light intensitites takes place when said different portions are successively interposed in said light path, said method further including the step of progressively moving the diffusing means until a contrast between the subject and its background reaches a threshold.

* * * * *